(12) United States Patent
Riach, Jr.

(10) Patent No.: US 6,616,595 B2
(45) Date of Patent: Sep. 9, 2003

(54) VORTEX MAGNETIC REGENERATING DEVICE

(76) Inventor: George Riach, Jr., P.O. Box 1134, Los Alamitos, CA (US) 90720

( * ) Notice: Subject to any disclaimer, the term of this patent is extended or adjusted under 35 U.S.C. 154(b) by 0 days.

(21) Appl. No.: 09/731,075

(22) Filed: Dec. 5, 2000

(65) Prior Publication Data

US 2002/0068847 A1 Jun. 6, 2002

Related U.S. Application Data

(60) Provisional application No. 60/229,970, filed on Sep. 1, 2000.

(51) Int. Cl.⁷ ................................................. A61N 2/00
(52) U.S. Cl. .......................................... 600/9; 335/209
(58) Field of Search ......................... 600/9–15; 335/209

(56) References Cited

U.S. PATENT DOCUMENTS

| | | | | | |
|---|---|---|---|---|---|
| 4,411,270 A | * | 10/1983 | Damadian | ................... | 128/653 |
| 5,035,017 A | * | 7/1991 | Komuro | ........................ | 5/481 |
| 5,105,490 A | * | 4/1992 | Shek | ............................. | 5/448 |
| 5,168,588 A | * | 12/1992 | Chan | ............................. | 5/448 |
| 5,226,185 A | * | 7/1993 | Guay et al. | ..................... | 5/448 |
| 5,304,111 A | * | 4/1994 | Mitsuno et al. | ................. | 600/9 |
| 5,307,039 A | * | 4/1994 | Chari et al. | ................. | 355/299 |
| 5,323,499 A | * | 6/1994 | Chan | ............................. | 5/448 |
| 5,993,375 A | * | 11/1999 | Engel | .......................... | 600/15 |
| 6,048,303 A | * | 4/2000 | Porter | ......................... | 600/15 |
| 6,169,963 B1 | * | 1/2001 | Markov | ....................... | 702/57 |
| D439,982 S | * | 4/2001 | Ruscitti | ..................... | D24/188 |
| 6,348,033 B1 | * | 2/2002 | Catlett | ......................... | 600/15 |
| 6,416,458 B1 | * | 7/2002 | Spiegler | ........................ | 600/9 |
| 6,418,345 B1 | * | 7/2002 | Tepper et al. | .................. | 607/51 |
| 6,436,020 B1 | * | 8/2002 | Weingand | .................... | 482/148 |
| 6,497,648 B1 | * | 12/2002 | Rey | ............................. | 600/14 |

FOREIGN PATENT DOCUMENTS

| | | | | |
|---|---|---|---|---|
| DE | 3325356 A1 | * | 1/1985 | ............ A61N/1/42 |
| DE | 40 09 069 A1 | * | 9/1991 | ............ A61F/13/00 |
| GB | 2 168 898 A | * | 7/1986 | ............ A61N/1/42 |
| JP | 404367666 A | * | 12/1992 | ............ A61N/2/08 |
| JP | 404367667 A | * | 12/1992 | ............ A61N/2/08 |
| JP | 406098941 A | * | 4/1994 | ............ A61N/2/08 |

* cited by examiner

Primary Examiner—Henry Bennett
Assistant Examiner—Nihir Patel
(74) Attorney, Agent, or Firm—Orum & Roth

(57) ABSTRACT

A vortex magnetic regenerating device uses magnetic fields focused by a magnetic keeper upon a user to assist in regeneration of a living being. A layered construction of a magnetic keeper, magnetic strips, a board surface all covered by a covering creates the magnetic vortex generating device which may be flipped one side of the other to expose the user to either positive or negative magnetic fields.

10 Claims, 3 Drawing Sheets

VORTEX MAGNETIC REGENERATING DEVICE

This application claims the benefit of U.S. Provisional Application No. 60/229,970 filed Sep. 1, 2000.

BACKGROUND OF THE INVENTION

The present invention relates to the basic and fundamental laws of earthly electric nature, gravity, the weak and strong magnetic forces, all directly related to our 100% electromagnetic, DNA molecular bodies comprised of charges, semi-solids, liquids, chemicals and gases in the form of energy, spent, gained, retained and maintained beyond the earth's normal over-all 0.5 gauss. Gauss being to magnetism as current is to electricity. The method includes a man made Vortex device, and man made magnetic Vortex Pads to help accelerate the stronger than earth's over-all 0.5 gauss current flow, in the form of either all North on one side of the Vortex Device and all South on the other side. Other embodiments include a man made Magnetic Vortex Device, bipolared all magnetic South on one side of the Vortex Device, all magnetic North on the other, where either side of the Vortex Device can be used separately by turning it over, so North-South or South-North, magnetized Vortex Pads accelerate the magnetic gauss for DNA Molecular regeneration. Natural and man made magnetic Vortexes are from a regenerating direct current (DC) flow, not degenerating, alternating current (AC) flow.

In natures designed earth, Vortexes accelerate a natural magnetic current flowing from the molten ferrite loadstone of the inner-iron-core of the earth outward, at the speed of light. Natural Vortexes of various sizes, large and small, weak and strong, exist on various parts of the earth.

The accelerated current flow from an earthly Vortex is commonly attributed to gold deposits or crystal deposits deep in the bowels of the earth, which accelerates the earthly magnetic current outward, splitting the North-South, polarity of the magnetic Vortex in half, much as the non-homogeneous earth at the block wall in the center of the earth, splits the magnetic polarity of the earth, North-South. The coldest parts of the earth, the North and South poles, due to the freezing temperatures, also act as an accelerating, Natural Current Flow Vortex and are the largest and strongest non-homogeneous free wireless electromagnetic fields on earth. In parts of Mongolia and Tibet it is believed by the inhabitants their long lifespan, documented scientifically to be anywhere from a hundred years of age to two hundred years of age is due to the Vortex Current Flow Effect.

Just a few of the Vortex documented in the United States are at Sedona, Ariz. and Goldmine, Oreg. These vortexes are aeronautically mapped out to be avoided in air flight, as it can cause problems with the instrumentation of in-flight aircraft. Vortexes are known to exist below many of the earth's oceans.

The present invention supplies a local, artificial vortex effect, similar to a natural vortex's ability to align a users cellular structure in a similar fashion as a Magnetic Resonance Imager, but without the imaging component.

SUMMARY OF THE INVENTION

The primary object of the present invention is to provide a new portable, uncomplicated, means, device and/or apparatus to help duplicate nature's known method of super charging our human DNA Molecular Mass, as a much more beneficial exacting science presently unknown to the majority of mankind.

Some of the main features of this new invention relate to Vortex Pads. Vortex Pads are easily transportable and movable accelerated Vortex Devices. Vortex pads can be formed from a magnetic keeper, with magnetic tape attached, which focuses the magnetic tapes magnetic flux upon a user. The vortex devices are a natural way to regenerate, detoxify, and charge human DNA in two different non-homogeneous polarities. They are a non-invasive, non-toxic, non-drug related, natural way to help rejuvenate the entire human body at rest, work or play.

DETAILED DESCRIPTION OF THE DRAWINGS

DETAILED DESCRIPTION OF INVENTION

Figure 1:
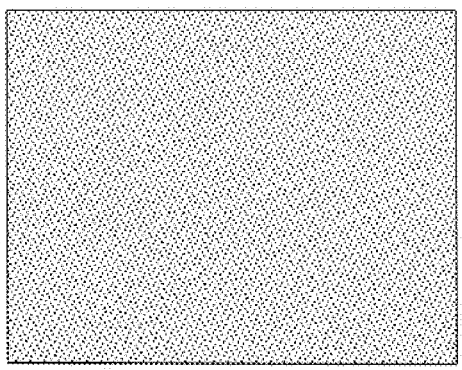
FIG. 1 is a representation of an uni-poled or bi-poled magnetic keeper.
Figure 2:
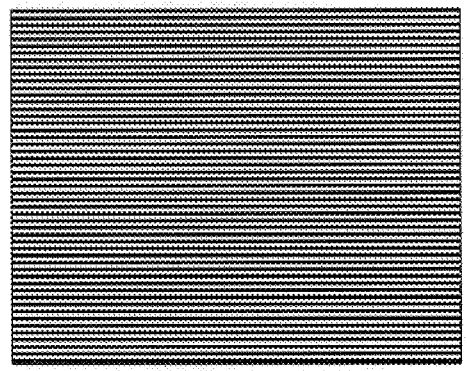
FIG. 2 is a representation of the uni-poled or bi-poled magnetic keeper with magnetic tape stripping attached.
Figure 5:
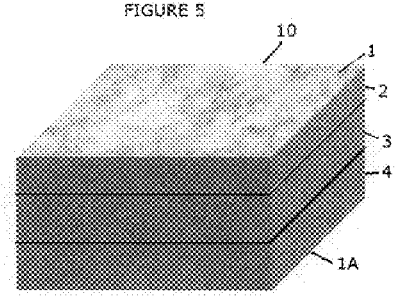
FIG. 5 is a representation of a layered construction of a vortex regenerating device.
Figure 6:
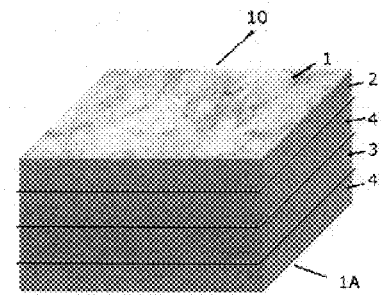
FIG. 6 is a representation of a layered construction of a vortex regenerating device with a magnetic keeper sandwich around the magnetic stripping.
Figure 8:
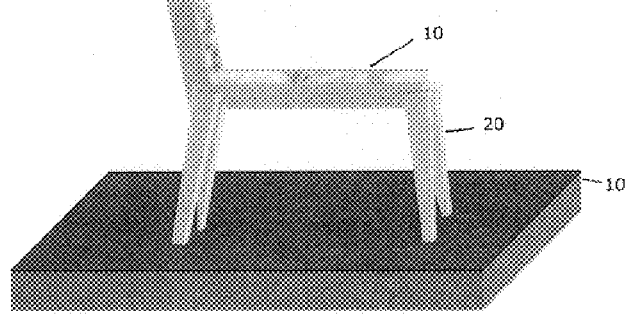
FIG. 8 is a representation of a Vortex (portable) regenerating device utilizing Vortex pads and a non-magnetic chair structure.

The Vortex Regenerating Device as shown in FIG. 8 is constructed of Vortex pads 10 and a non-magnetic chair structure 20. The chair structure 20 may be constructed of any non-ferrite material, or metal material formed so as to not obstruct or deter magnetic flux or preferably, plastic. The Vortex pads 10 may be alternatively constructed as shown in FIG. 5. The Vortex pads 10 are constructed from a ferro alloy, iron, steel, tin, ferrite, or other ferro magnetic material used to make up a uni-poled or bi-poled magnetic keeper 4 as shown in FIG. 1. Coating or galvanization of the keeper material may be applied to prevent oxidation. Galvanized Flashing RV14 available from Home Products Inc. of Lancaster, PA 15 a suitable keeper material. Thicker or thinner gauges of keeper material may be used. Upon the keeper 4, a single or multiple layer of magnetic tape 3 stripping is attached, preferably glued, as shown in FIG. 2. The keeper 4 focuses the magnetic flux upon the user, orienting the flux paths of the magnetic tape 3 stripping to act in a homogeneous additive fashion rather than individually. The magnetic tape 3 stripping in concert with the keeper 4 has been found to be superior to strip magnets or individual magnets without a keeper 4. The keeper 4 assists in maintaining the magnetic flux over time, protecting the vortex pad 10 from degradation. The strip magnets 3, preferably 1" or more in width, may be arranged in an adjacent parallel configuration or in an overlapping crisscross pattern. If sheet magnets are used, once in place, they should preferably be scored into parallel strips. This will assist in aligning the magnetic flux distribution. In another embodiment, as shown in FIG. 6, the keeper 4 is layered top and bottom, sandwiching the magnetic tape 3 on both sides. Synthetic material, such as flooring tile or linoleum material may be used to sandwich the magnetic tape 3 between the keeper 4. Use of Acrylic or other high impact plastic for the board surface 2 allows the use of product identification and display graphics, viewable through but protected by the board surface 2. Where this is used, the vinyl or other covering 1 is not used. Tape may be applied to protect exposed edges of the Vortex pad.

Figure 3:
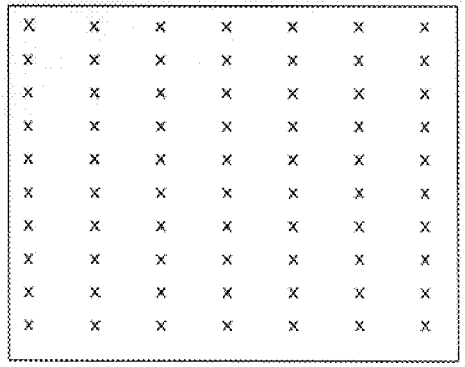
FIG. 3 is a representation of a board surface with the X symbol representing a north magnetic field flowing through the board surface.
Figure 4:
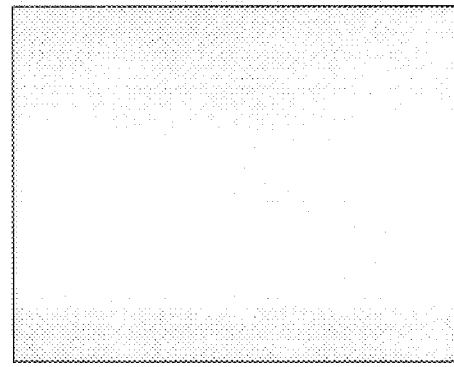
FIG. 4 is a representation of a covering for the board surface of FIG. 3.

A board surface 2 is next layered onto the Vortex pad 10 as shown in FIG. 3. The board surface 2 provides an economical means of providing structural rigidity to the vortex pad 10, especially if a thin gauge material keeper 4 is used. Depending on the type and thickness of the keeper 4 material, this may or may not be required. The board surface may alternatively provide a cushion for the user's comfort. The board surface 2 may be, for example, common gypsum board, wood, fiberboard, acrylic, plastic, ceramic or closed or open cell foam. Any material which does not impede the magnetic field is useable. The magnetic field from the magnetic tape 3 emanates through the board surface with the magnetic north facing up represented by X is as shown in FIG. 3. FIG. 4 shows a covering 1 for the Vortex pad 10. The covering 1 may be a sealed vinyl or a woven, for example nylon, cover for the Vortex pad 10. As shown in FIG. 5, the metal keeper 4 with magnetic tape 3 stripping glued or otherwise attached and board surface 2 with vinyl or other covering 1 creates a Vortex pad 10.

Figure 7:
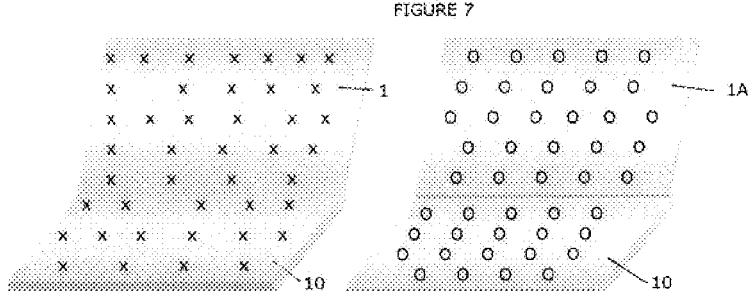
FIG. 7 is a representation of a vinyl-enclosed vortex regenerating seat and back pad adaptable to a seated, standing or laying position. Alternate positions of the pad, allowing either a north magnetic effect represented by X or a south magnetic effect represented by circles, are shown.

Two or more separate vortex pads may be joined in the same covering 1. This allows a hinge action between the two vortex pads, useful as a seat bottom and seat back, having any angle between them, in one easy to use foldable product. The Vortex pad 10 of FIG. 5 may be used in this embodiment as shown in FIG. 7 with either a north magnetic effect or reversed for a south magnetic effect, depending on whether a north surface 1 is exposed to the user or the south surface 1a is exposed to the user.

As shown in FIG. 8, the Vortex pads may be used in a chair structure and additionally at the foot area of the user below the chair structure. An additional Vortex pad may be used either under the user's feet or underneath the full area of the chair and user. A vortex pad 10 designed for use under chair legs will have a proportionately stronger board surface 2 so that the concentrated weight transmitted through the chair legs will not damage the vortex pad. Also, the magnetic stripping 2 may be of a higher gauss, for example obtained by multiple crisscrossing layers of magnetic tape 3 stripping.

Figure 9:
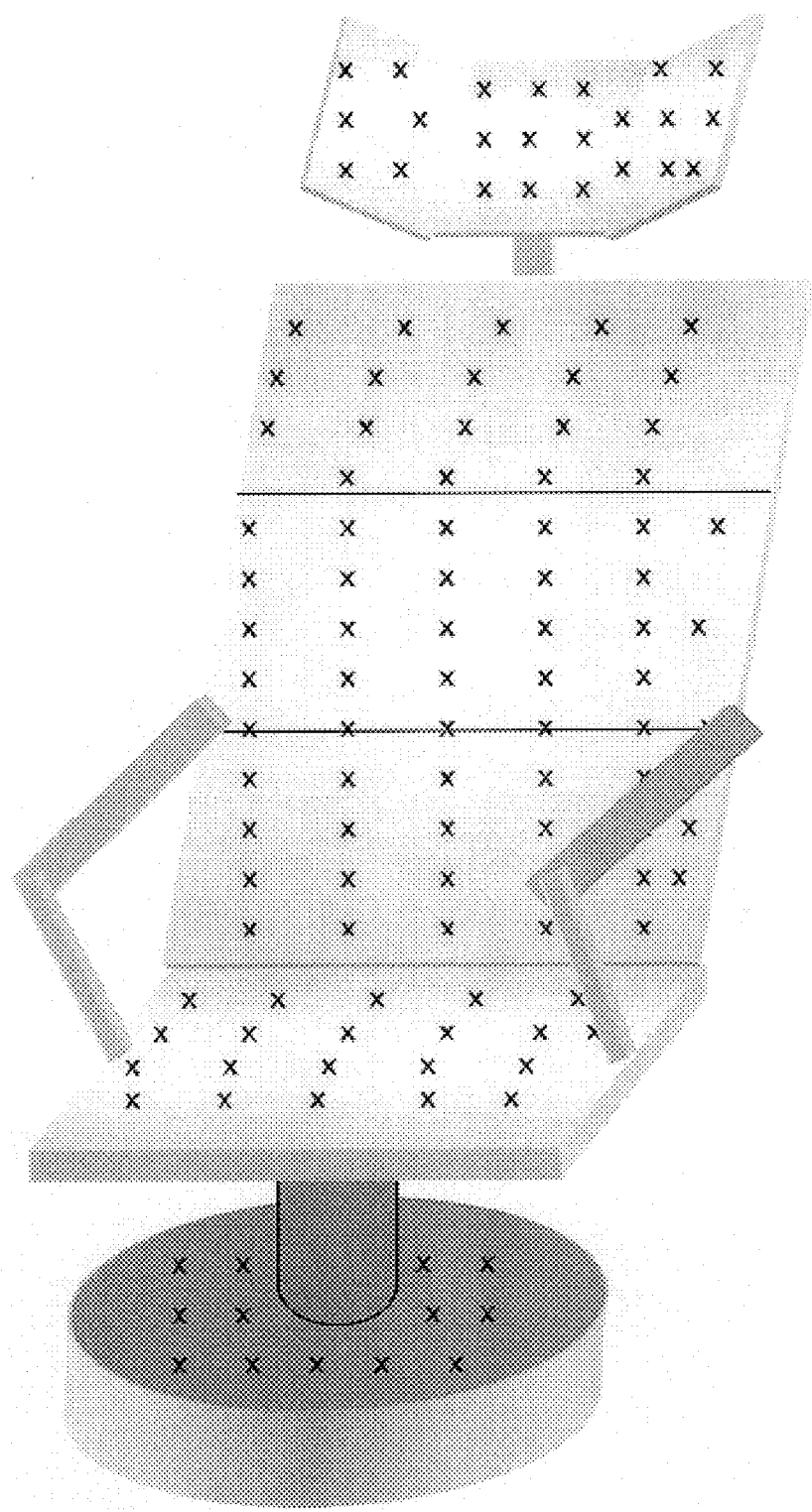
FIG. 9 is a representation of a Vortex regenerating chair with head and extended back supports.

In another embodiment, the vortex pads 10 may be designed into the backs and seats of chairs, stools, benches, beds. FIG. 9 shows a vortex chair with surrounding headrest and support base all having Vortex pads 10 creating a north projecting magnetic field directed to the user. This invention is useable in any manner where the magnetic field can be localized for beneficial effect on a living being's cellular structure, all tied into the unseen and unobvious laws of nature.

Magnetic field strength, gauss may be increased by using various gauss strengths of magnetic tapes or reduced accordingly to acquire the desired effect, more ordered oxygen and negative ions released naturally from the water of the users blood.

The range of magnetic flux extends from 0.5. gauss of earth's natural magnetic field to any higher man made means, creating the Vortex effect.

The present invention is entitled to a range of equivalents, and is to be limited only by the scope of the following claims.

I claim:

1. A vortex regenerating device comprising:

more than one magnetic keeper, said magnetic keepers each having an upper surface with a planar configuration and at least one permanent magnet having a magnetic polarity;

each said magnetic keeper and its respective at least one magnet arranged and constructed with said at least one magnet's magnetic polarity generally perpendicular to said magnetic keeper; and said magnetic keepers hingedly interconnected by a hinge means to allow placement upon a chair structure having a chair seat and a chair back with the magnetic keepers matching the angle of said chair seat and said chair back.

2. A device as claimed in claim 1, wherein the hinge means is a flexible portion of a covering enclosing each magnetic keeper.

3. A vortex regenerating device comprising:

a magnetic keeper having an upper surface with a planar configuration and at least one permanent magnet having a magnetic polarity;

said at least one magnet substantially covers at least one side of said magnetic keeper;

said at least on magnet and said magnetic keeper arranged and constructed with said at least one magnet's magnetic polarity generally perpendicular to said magnetic keeper; and said at least one magnet is divided into parallel magnetic strips.

4. The device as claimed in claim 3, wherein;

there is more than one layer of said parallel magnetic strips.

5. A vortex regenerating device comprising:

a magnetic keeper having an upper surface with a planar configuration and at least one permanent magnet having a magnetic polarity;

said at least one magnet and said magnetic keeper arranged and constructed with said at least one magnet's magnetic polarity generally perpendicular to said magnetic keeper; and wherein at least one magnet has a magnetic flux and said magnetic keeper focuses the magnetic flux.

6. A vortex regenerating device comprising:

a magnetic keeper having an upper surface with a planar configuration and at least one permanent magnet having a magnetic polarity;

said at least one magnet and said magnetic keeper arranged and constructed with said at least one magnet's magnetic polarity generally perpendicular to said magnetic keeper, said at least one magnet is a magnetic tape strip; and wherein said at least one magnet has a magnetic flux and said magnetic strip aligns the magnetic flux.

7. The device of claim 3, wherein at least one magnet has a magnetic flux and said magnetic strips align the magnetic flux.

8. A vortex regenerating device comprising:

a magnetic keeper having a planar configuration, and at least one magnet having a magnetic polarity; and said at least one magnet and said magnetic keeper arranged and constructed with said at least one magnet's magnetic polarity generally perpendicular to said magnetic keeper;

wherein said at least one magnet substantially covers at least one side of said magnetic keeper and said at least one magnet is divided into parallel magnetic strips.

9. The device as claimed in claim 8, wherein at least one magnet has a magnetic flux and said magnetic strips align the magnetic flux.

10. The device as claimed in claim 8, wherein there is more than one layer of said parallel magnetic strips.

* * * * *